(12) United States Patent
Kruger et al.

(10) Patent No.: US 12,427,051 B2
(45) Date of Patent: Sep. 30, 2025

(54) DYNAMICALLY ADJUSTING MANDIBULAR ADVANCEMENT DEVICES AND SYSTEMS

(71) Applicant: The Regents of the University of Michigan, Ann Arbor, MI (US)

(72) Inventors: Grant H. Kruger, Yipsilanti, MI (US); Neeraj Kaplish, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 210 days.

(21) Appl. No.: 18/044,004

(22) PCT Filed: Sep. 3, 2021

(86) PCT No.: PCT/US2021/048969
§ 371 (c)(1),
(2) Date: Mar. 3, 2023

(87) PCT Pub. No.: WO2022/051566
PCT Pub. Date: Mar. 10, 2022

(65) Prior Publication Data
US 2023/0329898 A1 Oct. 19, 2023

Related U.S. Application Data

(60) Provisional application No. 63/074,746, filed on Sep. 4, 2020.

(51) Int. Cl.
*A61F 5/56* (2006.01)
*A61B 5/00* (2006.01)
*A61B 5/1455* (2006.01)

(52) U.S. Cl.
CPC .......... *A61F 5/566* (2013.01); *A61B 5/14552* (2013.01); *A61B 5/4836* (2013.01); *A61B 5/682* (2013.01)

(58) Field of Classification Search
CPC ................. A61F 5/56–58; A61B 5/145; A61B 5/1455–14552; A61B 5/48;
(Continued)

(56) References Cited

U.S. PATENT DOCUMENTS

| 8,613,283 B2 | 12/2013 | Hegde et al. |
| 2009/0078273 A1 | 3/2009 | Bhat et al. |

(Continued)

FOREIGN PATENT DOCUMENTS

WO  WO 2019/185671  10/2019

OTHER PUBLICATIONS

International Search Report and Written Opinion for PCT/US2021/048969. Mailed Dec. 16, 2021. 12 pages.
(Continued)

*Primary Examiner* — Michelle J Lee
(74) *Attorney, Agent, or Firm* — Jason R. Bond; Casimir Jones, S.C.

(57) ABSTRACT

The present invention relates to methods, devices, and systems for dynamically adjusting mandibular advancement. In certain embodiments, the devices and systems employ actuator assemblies configured to allow a subject's lower jaw to be advanced by a minimum amount (e.g., trigged by obstructive sleep apnea (OSA) or associated significant oxygen saturations), but still allow the subject to move their jaw further forward, laterally, and open/close on their own. In some embodiments, the devices and systems employ an oxygen saturation measuring sensor linked to a motor control processor that: i) advances extending shafts forward when the oxygen saturation measuring sensor detects significant changes to oxygen saturation levels or other conditions that may signal OSA (e.g. a signal from another sleep monitoring device), and ii) retract the extending shafts backwards when the oxygen saturation measuring
(Continued)

sensor detect normal oxygen saturation levels or other condition is met (e.g. elapsed time, head position, etc.).

20 Claims, 8 Drawing Sheets

(58) Field of Classification Search
CPC ....... A61B 5/4836; A61B 5/68; A61B 5/6801; A61B 5/6813; A61B 5/6814; A61B 5/682; A61C 7/08; A61C 7/36; A63B 71/08–10
See application file for complete search history.

(56) References Cited

U.S. PATENT DOCUMENTS

| | | | |
|---|---|---|---|
| 2014/0135868 A1 | 5/2014 | Bashyam | |
| 2016/0199215 A1 | 7/2016 | Kopelman | |
| 2016/0324681 A1* | 11/2016 | Flanagan | A61F 5/566 |
| 2018/0263806 A1 | 9/2018 | Toussaint | |
| 2019/0328574 A1 | 10/2019 | Flanagan | |
| 2019/0343675 A1 | 11/2019 | Giridharagopalan et al. | |

OTHER PUBLICATIONS

Catchside. Predictors of continuous positive airway pressure adherence. F1000 Med Rep. Sep. 23, 2010:2:70. 6 pages.

Chen et al., Polysomnographic predictors of persistent continuous positive airway pressure adherence in patients with moderate and severe obstructive sleep apnea. Kaohsiung J Med Sci. Feb. 2015;31(2):83-9.

Clark et al., A crossover study comparing the efficacy of continuous positive airway pressure with anterior mandibular positioning devices on patients with obstructive sleep apnea. Chest. Jun. 1996;109(6):1477-83.

De Vries et al., Continuous positive airway pressure and oral appliance hybrid therapy in obstructive sleep apnea: patient comfort, compliance, and preference: a pilot study. Journal of Dental Sleep Medicine. 2016;3(1):5. 6 pages.

Dinapoli. Strategies to improve continuous positive airway pressure compliance: A review. Journal of Nursing Education and Practice. 2014;4(7):10. 11 pages.

Engleman et al., Improving CPAP use by patients with the sleep apnoea/hypopnoea syndrome (SAHS) Sleep Med Rev. Feb. 2003;7(1):81-99.

Fernandes et al., Understanding the shape-memory alloys used in orthodontics. ISRN Dent. 2011:2011:132408. 7 pages.

Fritsch et al., Side effects of mandibular advancement devices for sleep apnea treatment. Am J Respir Crit Care Med. Sep. 1, 2001;164(5):813-8.

Groza. Sleep apnea local networks: bridging the communication gaps. Journal of Dental Sleep Medicine. 2015;2(2):1. 59.

Harvard Medical School. Price of Fatigue: The Suprising Economic Costs of Unmanaged Sleep Apnea. McKinsey and Harvard Medical School, 2010. 33 pages.

Jean-Louis et al., Obstructive sleep apnea and cardiovascular disease: evidence and underlying mechanisms. Minerva pneumologica. 2009;48(4):277-93.

Mehra et al., Association of nocturnal arrhythmias with sleep-disordered breathing: The Sleep Heart Health Study. Am J Respir Crit Care Med. Apr. 15, 2006;173(8):910-6.

Napankangas et al., Effect of mandibular advancement device therapy on the signs and symptoms of temporomandibular disorders. J Oral Maxillofac Res. Jan. 1, 2013;3(4):e5. 8 pages.

Pantin et al., Dental side effects of an oral device to treat snoring and obstructive sleep apnea. Sleep. Mar. 15, 1999;22(2):237-40.

Punjabi. The epidemiology of adult obstructive sleep apnea. Proc Am Thorac Soc. Feb. 15, 2008;5(2):136-43.

Schmidt-Nowara et al., Oral appliances for the treatment of snoring and obstructive sleep apnea: a review. Sleep. Jul. 1995;18(6):501-10.

Sutherland et al., Oral appliance treatment for obstructive sleep apnea: an update. J Clin Sleep Med. Feb. 15, 2014;10(2):215-27.

Victor. Treatment of obstructive sleep apnea in primary care. Am Fam Physician. Feb. 1, 2004;69(3):561-8.

Wittmann et al., Health care costs and the sleep apnea syndrome. Sleep Med Rev. Aug. 2004;8(4):269-79.

Young et al., Epidemiology of obstructive sleep apnea: a population health perspective. Am J Respir Crit Care Med. May 1, 2002;165(9):1217-39.

* cited by examiner

FIG. 1A
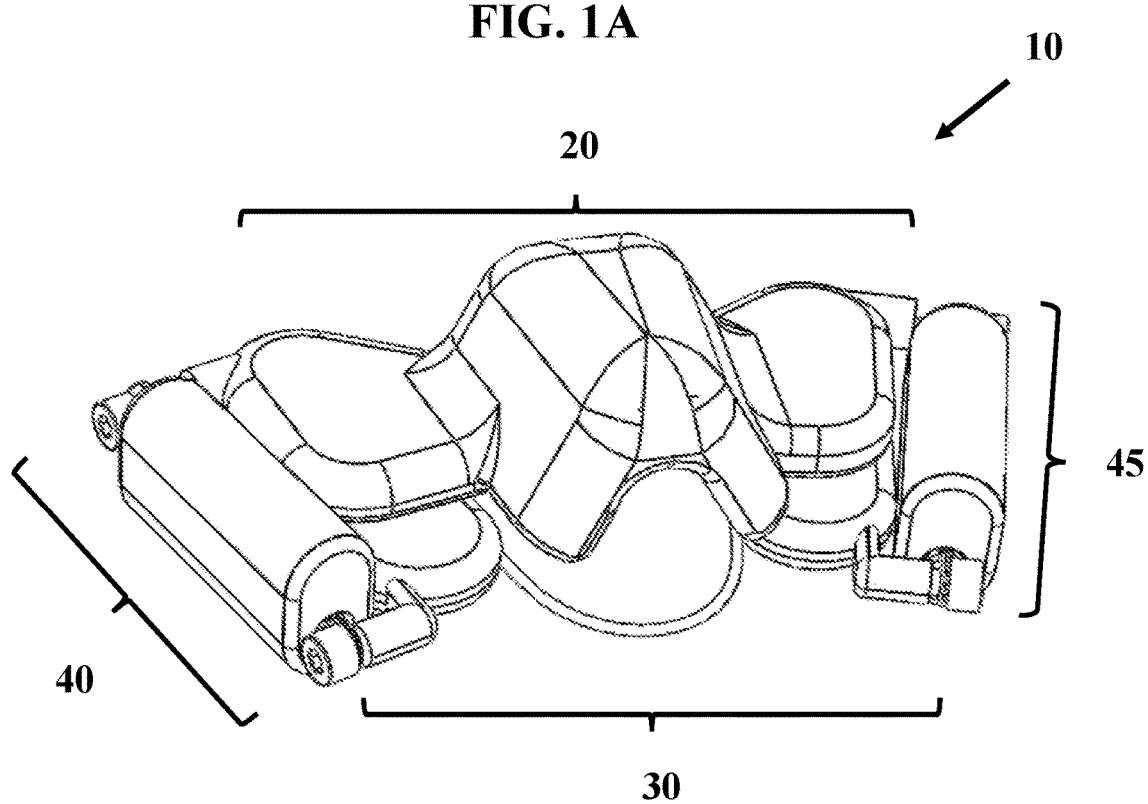
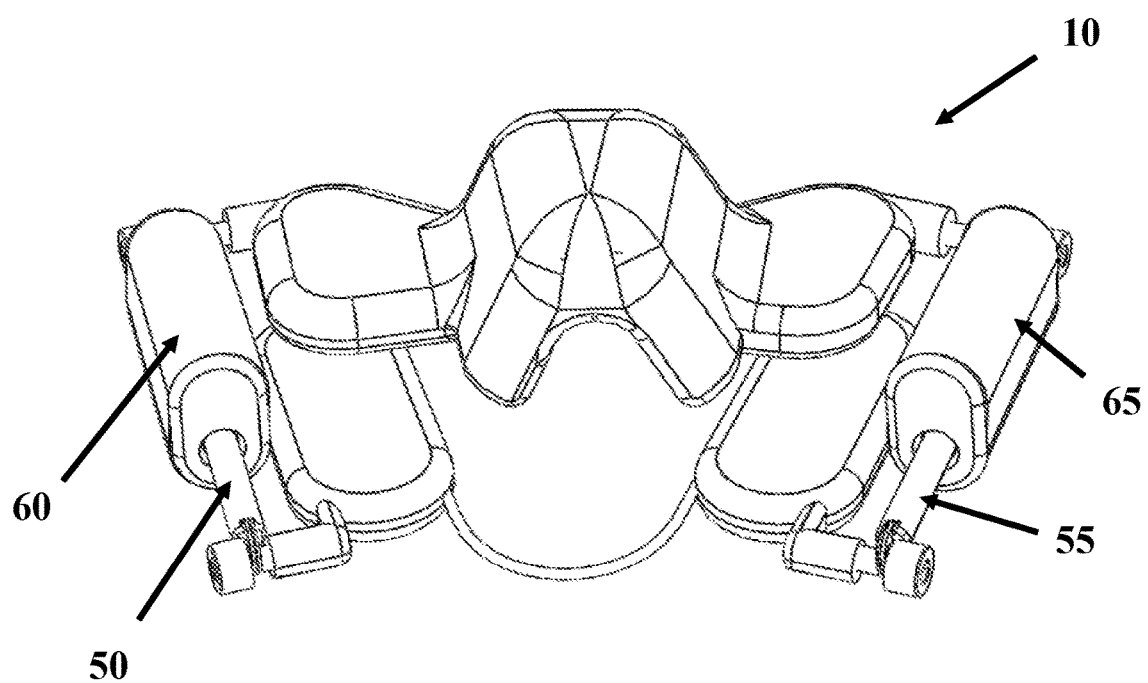
FIG. 1B

FIG. 3A
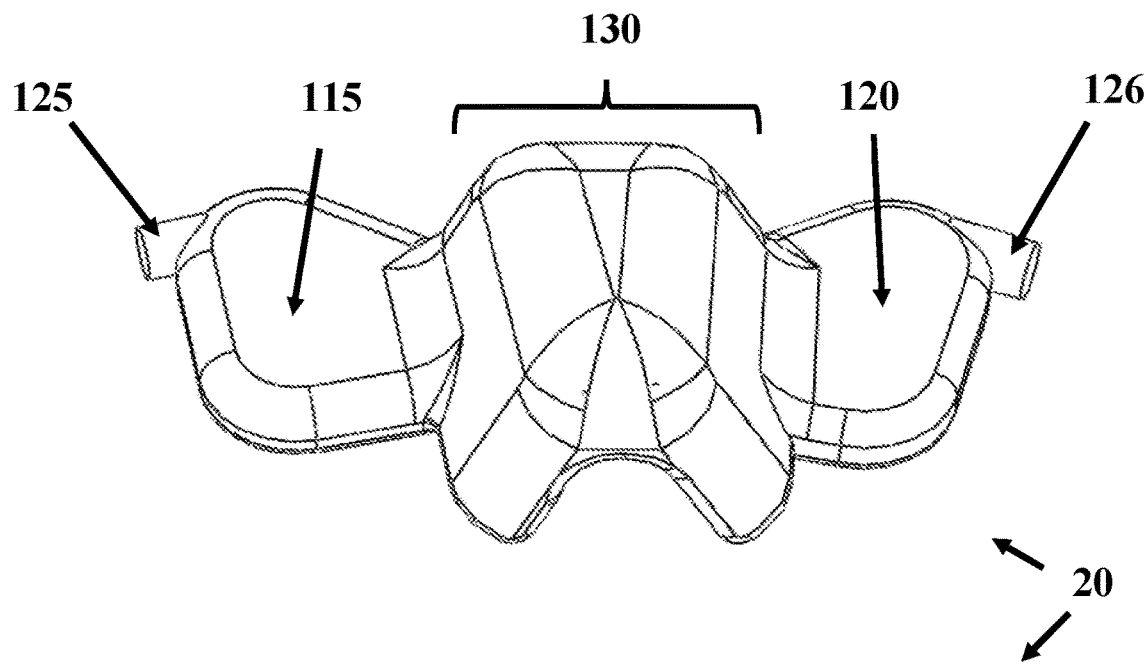
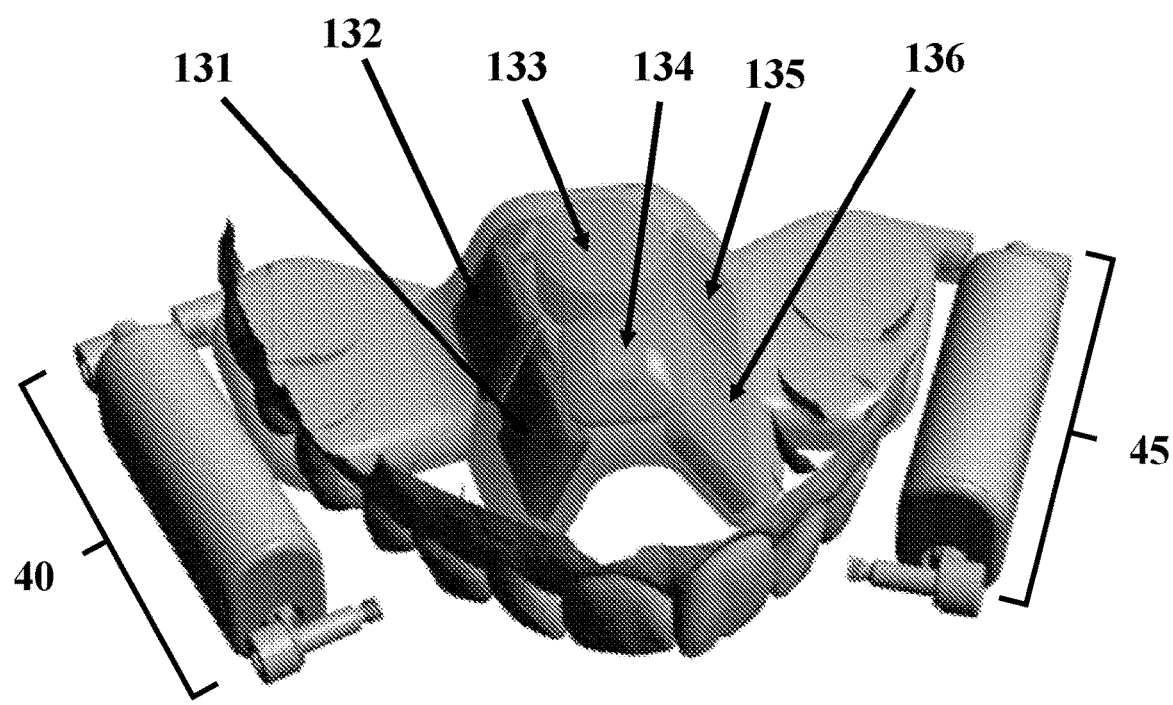
FIG. 3B

DYNAMICALLY ADJUSTING MANDIBULAR ADVANCEMENT DEVICES AND SYSTEMS

The present application claims priority to U.S. Provisional application Ser. No. 63/074,746 filed Sep. 4, 2021, which is herein incorporated by reference in its entirety.

FIELD OF THE INVENTION

The present invention relates to methods, devices, and systems for dynamically adjusting mandibular advancement. In certain embodiments, the devices and systems employ actuator assemblies configured to allow a subject's lower jaw to be advanced by a minimum amount (e.g., triggered by obstructive sleep apnea (OSA) or associated significant oxygen saturations), but still allow the subject to move their jaw further forward, laterally, and open/close on their own. In some embodiments, the devices and systems employ an oxygen saturation measuring sensor linked to a motor control processor that: i) advances extending shafts forward when the oxygen saturation measuring sensor detects significant changes to oxygen saturation levels or other conditions that may signal OSA (e.g. a signal from another sleep monitoring device), and ii) retract the extending shafts backwards when the oxygen saturation measuring sensor detect normal oxygen saturation levels or other condition is met (e.g. elapsed time, head position, etc.). In particular embodiments, the upper and lower teeth anchors employed with the systems and devices only each cover between one and three of the subject's teeth.

BACKGROUND OF THE INVENTION

Obstructive sleep apnea (OSA) is a sleeping disorder that has affected 25 million Americans in 2014 [1]. It usually occurs when the muscles in the upper airway relax too much during sleep especially Rapid Eye Movement (REM) sleep. This muscle relaxation causes the back of the tongue to collapse and obstruct the airway. OSA leads to low blood oxygen levels or sleep fragmentation and brief arousals which reopens the airway. A patient that suffers from OSA therefore usually cannot enjoy prolonged, deep sleep. OSA can also lead to high blood pressure, heart attack, stroke, and cardiac arrhythmias.

Surgical options for curing OSA exist, but each are invasive and not sought after. Patients instead prefer non-invasive treatment devices such as continuous positive airway pressure (CPAP) machines, which deliver pressurized air through a face mask to keep the airway open. Should CPAP therapy not be tolerated by the patient another option are to employ tongue retaining devices (TRDs) and mandibular advancement devices (MADs), which are worn orally to hold either the tongue forward or advance the lower jaw; Unfortunately each of these devices are uncomfortable to use; CPAP machines are cited as too loud and their face masks cause discomfort; TRDs are difficult to become accustomed to and may be uncomfortable; MADs currently on the market are static, requiring the manual advancement of the mandible prior to sleep in a position that will remain unchanged for the entire sleep duration. Some patients have experienced teeth movement and jaw muscle soreness.

SUMMARY OF THE INVENTION

The present invention relates to methods, devices, and systems for dynamically adjusting mandibular protrusion. In certain embodiments, the devices and systems employ actuator assemblies configured to allow a subject's lower jaw to be advanced by a minimum amount (e.g., trigged by obstructive sleep apnea and associated with significant oxygen saturations or arousals), but still allow the subject to move their jaw further forward and laterally on their own. In some embodiments, the devices and systems employ an oxygen saturation measuring sensor linked to a motor control processor that: i) advances extending shafts forward when the oxygen saturation measuring sensor detects a significant oxygen desaturations, and ii) retract the extending shafts backwards when the oxygen saturation measuring sensor detect normal oxygen saturation levels. In particular embodiments, the upper and lower teeth anchors employed with the systems and devices only each cover between one and three of the subject's teeth.

In some embodiments, provided herein are mandibular advancement systems comprising: a) an upper oral component comprising: i) RHS (right hand side) and LHS (left hand side) upper teeth anchors that: A) each secure to at least one of the subject's upper teeth, and B) are each attached to, or integral with, an anchor connector, ii) an arch component connecting the RHS and LHS upper teeth anchors, and iii) a plurality of electrical components comprising: A) an energy storage assembly, B) a wireless communications and signal processor, C) at least one motor power control module: b) a lower oral component comprising: i) RHS and LHS lower teeth anchors that: A) each secure to at least one of the subject's lower teeth, and B) are each attached to, or integral with, an anchor connector, and ii) a bridge component connecting the RHS and LHS lower teeth anchors; and c) first and second actuator assemblies each comprising: i) a housing comprising: A) a plurality of walls defining an internal cavity, B) a front aperture, and C) a housing connector configured to attach to one of the rear anchor connectors directly or indirectly, and ii) a plurality of housing components comprising: A) a motor, B) a gear assembly, C) a linear actuator, D) an extending shaft and E) a nut mounted on the linear actuator, and F) a shaft connector operably linked to the extending shaft and configured to attach to one of the anchor connectors directly or indirectly; and wherein the mandibular advancement system, when installed in a subject's mouth and when the actuator connecters are attached to the shaft and housing connectors respectively, is configured to move the subject's lower jaw forward past the upper jaw a minimum amount. In certain embodiments, the minimum amount is set by the position of the extending shaft and nut on the linear actuator, when the extending shafts move away from the housing.

In certain embodiments, provided herein are mandibular advancement systems comprising: a) an upper oral component comprising: i) RHS (right hand side) and LHS (left hand side) upper teeth anchors that: A) each secure to at least one of the subject's upper teeth, and B) are each attached to, or integral with, a rear anchor connector, ii) an arch component connecting the RHS and LHS upper teeth anchors, and b) a plurality of electrical components comprising: i) a power storage unit, ii) a wireless signal processor, and iii) at least one motor power control processor: c) a lower oral component comprising: i) RHS and LHS lower teeth anchors that: A) each secure to at least one of the subject's lower teeth, and B) are each attached to, or integral with, a front anchor connector; and d) first and second actuator assemblies each comprising: i) a housing comprising: A) a plurality of walls defining an internal cavity, B) a front aperture, and C) a housing connector configured to attach to one of the rear anchor connectors directly or indirectly, and ii) a plurality of housing components comprising: A) a motor, B) a gear assembly, C) a linear actuator, D) an extending shaft, and E) a shaft connector operably linked to the extending shaft and configured to attach to one of the front anchor connectors directly or indirectly; and wherein the mandibular advancement system, when installed in a subject's mouth and when the front and rear anchor connecters are attached to the shaft and housing connectors respectively, is configured to move the subject's lower teeth forward past the upper teeth a minimum amount when the extending shafts move away from the housing.

In certain embodiments, provided herein are systems or devices comprising the first and/or second actuator assemblies described herein.

In some embodiments, the plurality of electrical components are attached to the arch component, and/or wherein the energy storage assembly comprises a battery assembly. In other embodiments, the plurality of electrical components further comprises an oxygen saturation measuring sensor. In other embodiments, the extending shaft is slidably mounted on the linear actuator. In additional embodiments, the linear actuator comprises a threaded shaft.

In certain embodiments, the at least one motor power control processor is configured to activate the motors to advance the extending shafts forward when: i) when an oxygen saturation measuring sensor detects lower than normal oxygen saturation levels in the subject, ii) an absolute or relative time interval is reached, or iii) a command is received from a remote device. In some embodiments, the systems further comprise the oxygen saturation measuring sensor, and/or the remote device.

In particular embodiments, the at least one motor power control processor is configured to activate the motors to allow the extending shafts to retract when: i) an oxygen saturation measuring sensor detects normal oxygen saturation levels in the subject, ii) an absolute or relative time interval is reached, iii) a command is received from a remote device. In other embodiments, the systems further comprise the oxygen saturation measuring sensor, and/or the remote device.

In particular embodiments, each of the anchor connectors is configured to attach to one of the upper or lower shaft connectors indirectly via one or more linkage components, and wherein the system further comprises the one or more linkage components. In further embodiments, the one or more linkage components comprise at least one pivot component. In other embodiments, the pivot component is selected from the group consisting of: rods, screws, pins, and rings. In some embodiments, the oxygen saturation measuring sensor comprises a photoplethysmography (PPG) sensor. In further embodiments, the oxygen saturation measuring sensor is configured to measure oxygen saturation in the subject's soft palette and/or gums. In additional embodiments, the oxygen saturation measuring sensor comprises a pulse oximeter which comprises: a light source, photo detectors, and is configured to transmit light through a translucent, pulsating arterial bed of the subject oral cavity.

In some embodiments, the systems further comprise electrical connectors connecting the plurality of electrical components and the motor, wherein the electrical connectors are selected from: a plurality of wires, cables, circuits, and pcb. In other embodiments, the housing components further comprise a retaining nut attached to the extending shaft that is larger in diameter than the extending shaft and that prevents the extending shaft from fully sliding out of the housing.

In particular embodiments, the mandibular advancement system, when installed and connected, is further configured to allow the subject to move their lower jaw further forward past the minimum amount, but not allow the subject to withdraw their lower jaw backwards past the minimum amount. In other embodiments, the mandibular advancement system, when installed and connected, is further configured to allow lateral movement of the subject's lower jaw. In other embodiments, the housing components further comprises a thrust bearing/shaft axial support configured to protect the housing from high axial loads.

In some embodiments, the RHS and LHS upper teeth anchors each comprise a plastic wing with a dental impression of between one and five of the subject's teeth, and wherein only between one and five of the subject's teeth are covered by each of the upper teeth anchors. In particular embodiments, the RHS and LHS upper teeth anchors each comprise a plastic wing with a dental impression of between two and three of the subject's teeth, and wherein only between two and three of the subject's teeth are covered by each of the upper teeth anchors. In further embodiments, the RHS and LHS upper teeth anchors each comprise at least one tooth clip. In other embodiments, the RHS and LHS lower teeth anchors each comprise a plastic wing with a dental impression of between one and five of the subject's teeth, and wherein only between one and five of the subject's teeth are covered by each of the lower teeth anchors. In particular embodiments, the RHS and LHS lower teeth anchors each comprise a plastic wing with a dental impression of between two and three of the subject's teeth, and wherein only between two and three of the subject's teeth are covered by each of the lower teeth anchors.

In some embodiments, the RHS and LHS lower teeth anchors each comprise at least one tooth clip. In further embodiments, the anchor connector is selected from the group consisting of: a tube that accepts a pin or rod, a pin, a rod, screw, clip, ring, or a ball and socket joint. In further embodiments, the linear actuator is selected from the group consisting of: a leadscrew, a ball screw; Acme screw, Roller screw and/or a rack and pinion system.

In some embodiments, the arch component is shaped to generally follow the contour the hard palate of the subject's oral cavity. In other embodiments, the arch component comprises a plastic material. In additional embodiments, the power storage unit comprises a battery and a wireless charging circuit. In additional embodiments, the power storage unit comprises a lithium polymer battery. In other embodiments, the power storage unit comprises a capacitor. In some embodiments, the wireless signal processor comprises a Bluetooth processor.

In certain embodiments, the motor is selected from a DC electric motor or a piezoelectric motor. In some embodiments, the piezoelectric motor comprises a piezoelectric SQUIGGLE motor. In other embodiments, the front anchor connector is selected from the group consisting of: a tube that accepts a pin or rod, a pin, a rod, screw, clip, ring or ball and socket joint. In other embodiments, the bridge component comprises a wire frame structure.

In certain embodiments, the plurality of walls comprises first and second side walls and first and second end walls. In other embodiments, the front aperture is in the first end wall and the housing connector is attached to, or integral with, the second end wall. In additional embodiments, the first and second end walls each comprise a removable cap. In other embodiments, the at least one motor power control processor comprises first and second motor power control processors each configured to control one of the motors.

In certain embodiments, the plurality of electrical components are inside between the arch component and/or the actuator housings. In additional embodiments, the gear assembly comprises a planetary gearbox. In further embodiments, the gear assembly comprises at least two spur gears. In other embodiments, the gear assembly comprises a planetary gear box and at least two spur gears. In some embodiments, the motor, the gear assembly, and the linear actuator are inside the internal cavity of the housing.

In particular embodiments, the shaft connector is selected from the group consisting of: a tube that accepts a pin or rod, a pin, a rod, a screw, clip, ring or ball and socket joint. In other embodiments, the plurality of electrical components further comprise: E) a capacitor. In additional embodiments, the capacitor comprises an electric double layer capacitor (EDLC).

In particular embodiments, the housing components further comprise a first O-ring seal at a first end of the internal cavity of the housing. In further embodiments, the housing components further comprise a second O-ring seal at a second end of the internal cavity of the housing. In other embodiments, each of the extending shafts are about 14-25 mm in length. In additional embodiments, the upper teeth anchors and/or the lower teeth anchors are composed of non-rigid material to allow at least some rotation and/or translation of the subject's upper or lower jaw. In further embodiments, the plurality of housing components further comprise a resistive strip that is positioned to have brush contact with the leadscrew or nut such that the resistive strip serves as a potentiometer for absolute position measurement of the leadscrew nut and/or the extending shaft. In some embodiments, the plurality of housing components further comprise a magnetic strip, or an optical, acoustic, inductive or capacitive components configured for determining the position of the shaft. In other embodiments, the plurality of housing components further comprises a component configured to count the number of shaft rotations or count the number of marks passed by the nut. In certain embodiments, the component comprises an ultrasound transducer configured to measure the time of flight between the housing wall and shaft/nut using successive pings.

In some embodiments, the nut is positioned within the internal cavity of the housing such that it is prevented from rotating when the leadscrew rotates. In further embodiments, the wireless signal processor is configured to transmit voltage, current, and/or oxygen saturation measurements to a computer program and/or smart phone app. In additional embodiments, the wireless signal processor is configured to receive commands from a computer program and/or smartphone app to advance or retract the extending shafts.

In other embodiments, the subject is a human. In some embodiments, the human has, or is suspected of having, obstructive sleep apnea. In further embodiments, the systems further comprise one or more potentiometers configured to measure position of each extending shaft.

DESCRIPTION OF THE DRAWINGS

FIG. 1A shows an exemplary mandibular advancement device (MAD) (10) composed of an upper oral component (20) and a lower oral component (30), which are operably connected by right hand side (RHS) actuator assembly (40) and left hand side (LHS) actuator assembly (45). FIG. 1B shows an exemplary mandibular advancement device (10) with the RHS extending shaft (50) and LHS extending shaft (55), protruding from the RHS actuator housing (60)) and LHS actuator housing (65) respectively. Such extension moves the lower oral component forward.

FIG. 3A shows an exemplary upper oral component (20) with a RHS upper teeth anchor (115) and a LHS upper teeth anchor (120) connected by arch component (130). FIG. 3A also shows the RHS rear anchor connector (125) and LHS rear anchor connector (126). FIG. 3B shows an exemplary upper oral component (20) with an arch component (130) containing, or attached to, the following components: i) wireless signal processor (131) (e.g., Bluetooth processor); ii) RHS motor power control unit (132); iii) battery assembly (133) (e.g., composed of a LiPo batter and wireless charging coil/circuit); iv) SpO2 sensor (134); v) LHS motor power control processor (135); and capacitor (e.g., electric double layer capacitor or "EDLC") (136). In certain embodiments, in alternatively, or in addition, and head position sensor and/or a snore sensor, is part of the system.

FIG. 4B also shows a RHS rear anchor connector (125) connected to a rear RHS pivot component, and a LHS rear anchor connector (126) connected to a rear LHS pivot component.

DETAILED DESCRIPTION OF THE INVENTION

The present invention relates to methods, devices, and systems for dynamically adjusting mandibular advancement devices and systems. In certain embodiments, the devices and systems employ actuator assemblies configured to allow a subject's lower jaw to be advanced by a minimum amount (e.g., trigged by obstructive sleep apnea and associated low oxygen saturation), but still allow the subject to move their jaw further forward and laterally on their own. In some embodiments, the devices and systems employ an oxygen saturation measuring sensor linked to a motor control processor that: i) advances extending shafts forward when the oxygen saturation measuring sensor detects lower than normal oxygen saturation levels, and ii) retract the extending shafts backwards when the oxygen saturation measuring sensor detect normal oxygen saturation levels. In particular embodiments, the upper and lower teeth anchors employed with the systems and devices only each cover between one and three of the subject's teeth.

Provided herein, in certain embodiments, are robotic mandibular advancement devices and systems that can detect obstructive sleep apnea (OSA) and dynamically advance the jaw to treat OSA symptoms, and relax the jaw when symptoms subside. In some embodiments, such systems and devices reduce the discomfort of traditional mandibular advancement devices and improve or replace the expensive lab sleep studies patients must go through to calibrate their traditional devices or CPAP machines. In certain embodiments, the mandibular advancement devices and systems herein are used to treat and/or monitor obstructive sleep apnea and snoring. In particular embodiments, the mandibular advancement devices and systems provide at least one advantage selected from: i) reducing discomfort from prolonged jaw advancement: ii) minimizing tooth movement: iii) improved aesthetics over TRDs/CPAP: iv) ability to track severity/frequency of OSA and compliance; and v) reducing the cost of sleep studies Certain exemplary, non-limiting, embodiments of the systems and device herein are described below, with particular reference to the figures.

Figure 1C:
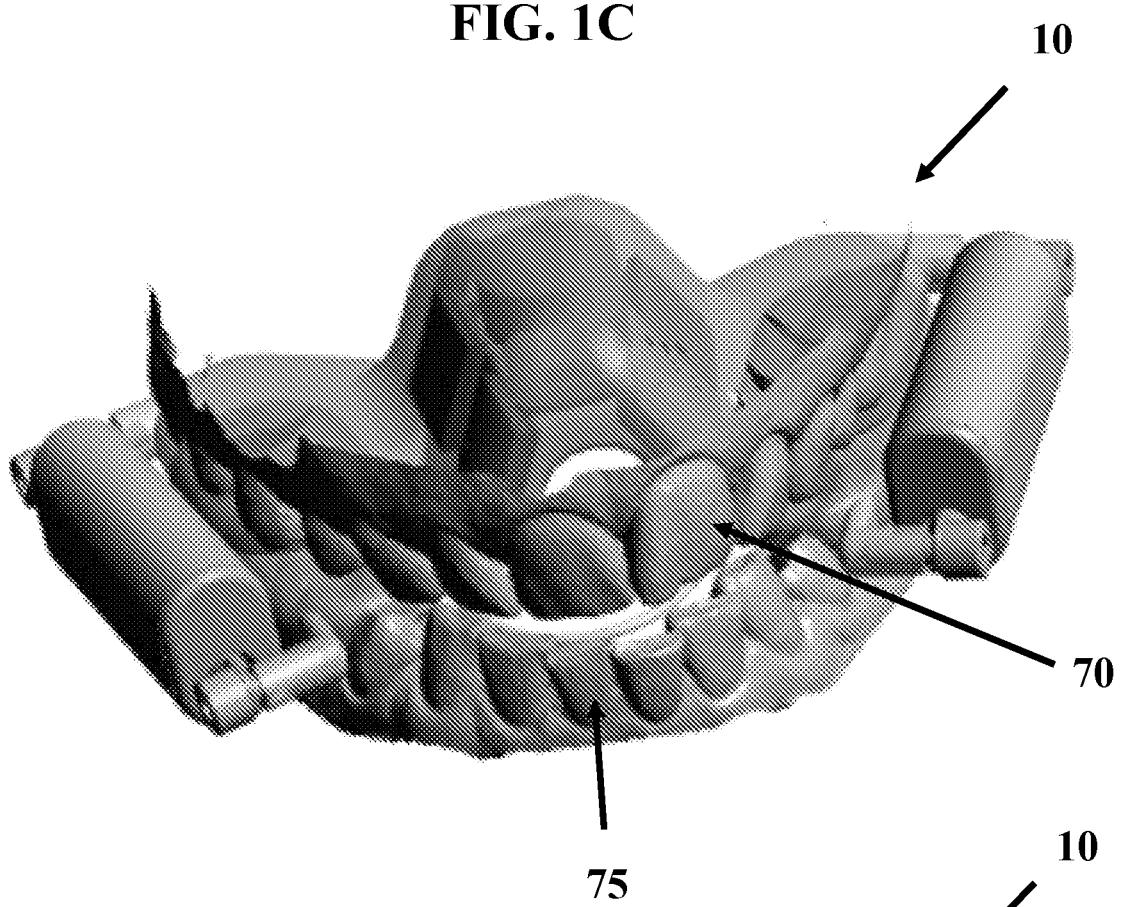
FIG. 1C shows an exemplary mandibular advancement device (10) in a subject's mouth in a non-extended position such that the upper set of teeth (70) are aligned with the lower set of teeth (75).
Figure 1D:
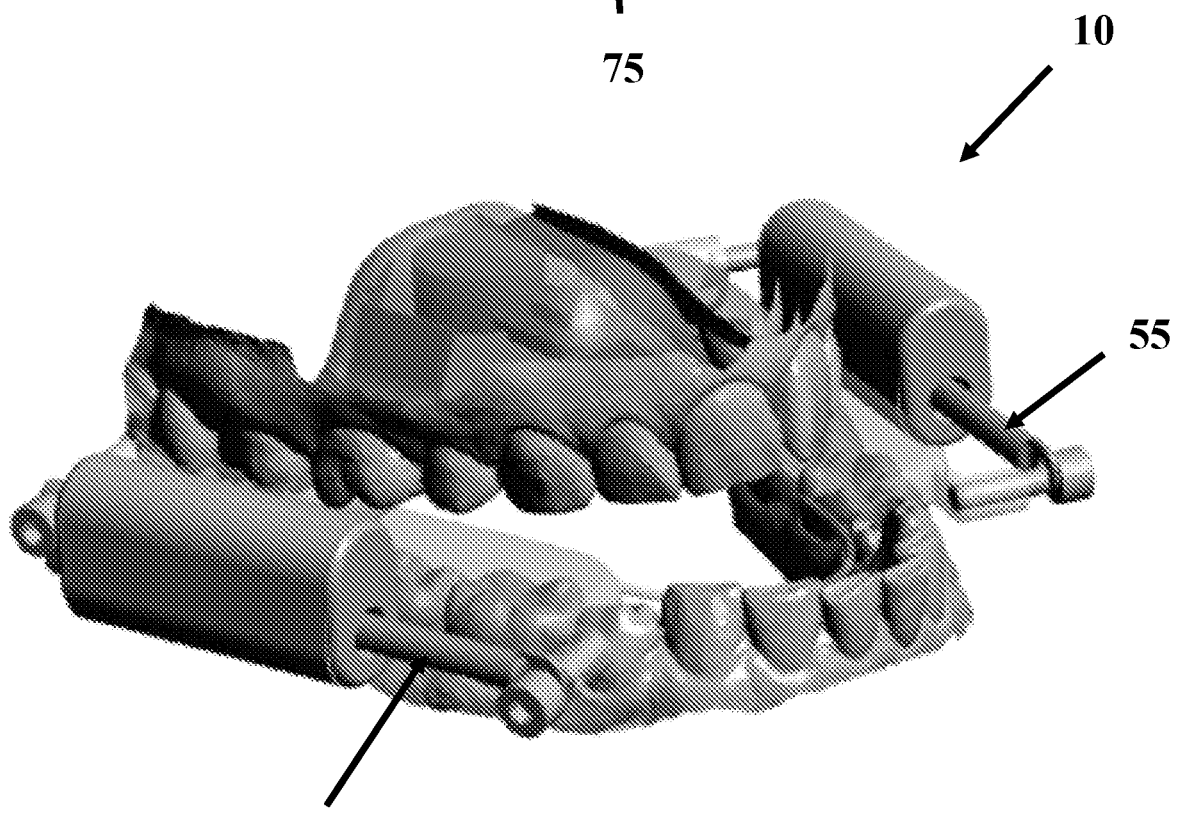
FIG. 1D shows an exemplary mandibular advancement device (10) in a subject's mouth in an extended position such that the lower set of teeth (75) and mandible are extended out past the upper teeth (70). This is accomplished by the RHS extending arm (50) and LHS extending arm (55) pushing forward, force the lower teeth (75) and mandible forward.

FIG. 1A shows an exemplary mandibular advancement device (MAD) (10) composed of an upper oral component (20) and a lower oral component (30), which are operably connected by right hand side (RHS) actuator assembly (40) and left hand side (LHS) actuator assembly (45). FIG. 1B shows an exemplary mandibular advancement device (10) with the RHS extending shaft (50) and LHS extending shaft (55), protruding from the RHS actuator housing (60) and LHS actuator housing (65) respectively. In certain embodiments, rather than an extending shaft, and extending screw or similar component is used. Such extension moves the lower oral component forward. FIG. 1C shows an exemplary mandibular advancement device (10) in a subject's mouth in a non-extended position such that the upper set of teeth (70) are aligned with the lower set of teeth (75). FIG. 1D shows an exemplary mandibular advancement device (10) in a subject's mouth in an extended position such that the lower set of teeth (75) and mandible are extended out past the upper teeth (70). In certain embodiments, the mandible is extended 1, 2, 3, or 3 mms. This is accomplished by the RHS extending arm (50) and LHS extending arm (55) pushing forward, force the lower teeth (75) and mandible forward. In some embodiments, the RHS and LHS extending shafts or screws are moved simultaneously. This can be accomplished, for example, by coordinated synchronization of the motion under microprocessor control.

Figure 2A:
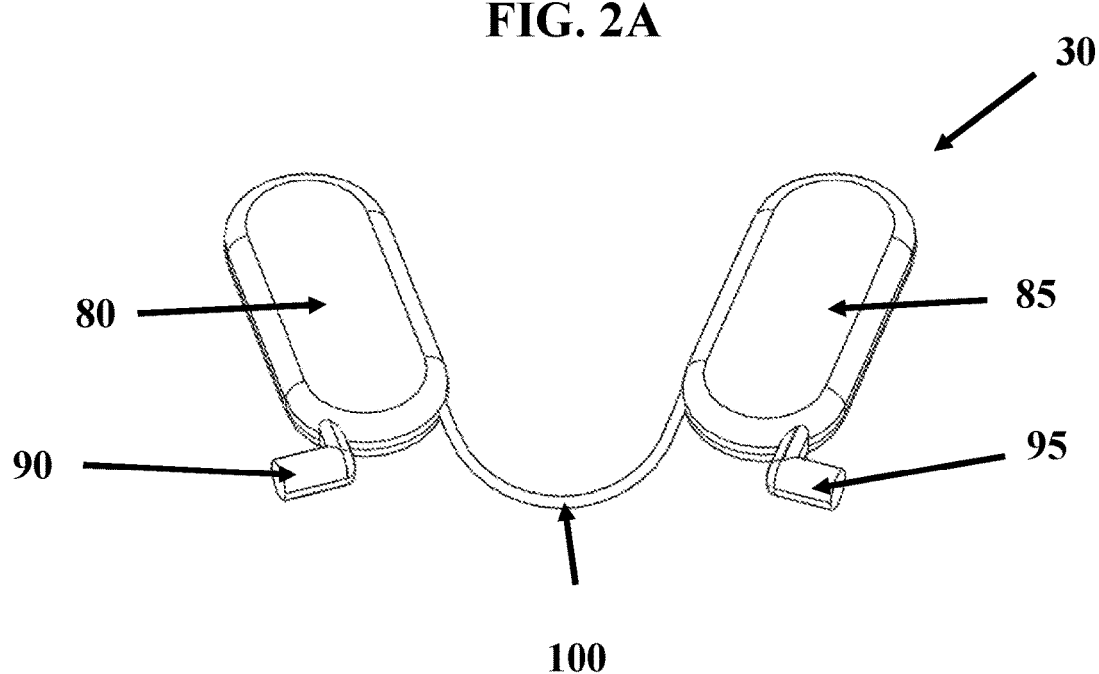
FIG. 2A shows an exemplary lower oral component (30) with a RHS lower teeth anchor (80) and a LHS lower teeth anchor (85) connected by a bridge component (100) (e.g., wire). A front anchor connector (90) is attached to (or integral with) the RHS teeth anchor (80), and a LHS front anchor connector (95) is attached to (or integral with) the LHS teeth anchor (85).
Figure 2B:
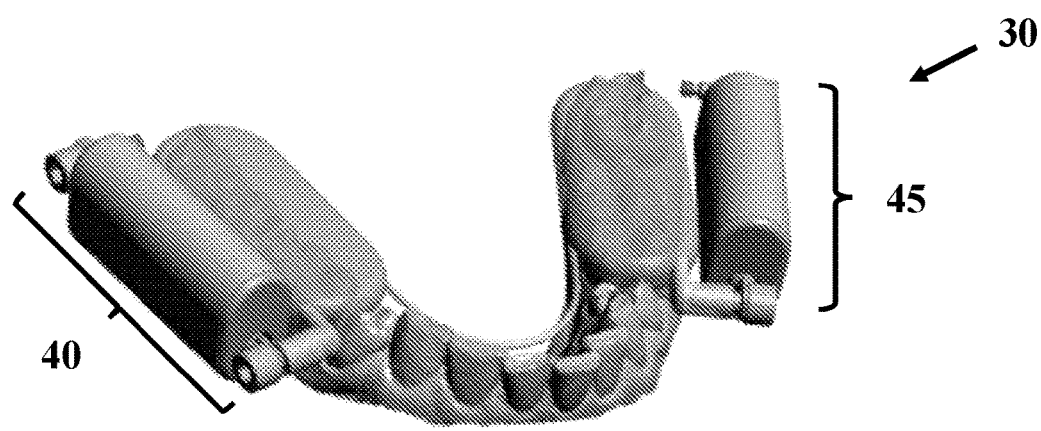
FIG. 2B shows an exemplary lower oral component (30) attached to a lower set of teeth, as well as a right hand side (RHS) actuator assembly (40) and left hand side (LHS) actuator assembly (45) attached thereto.
Figure 2C:
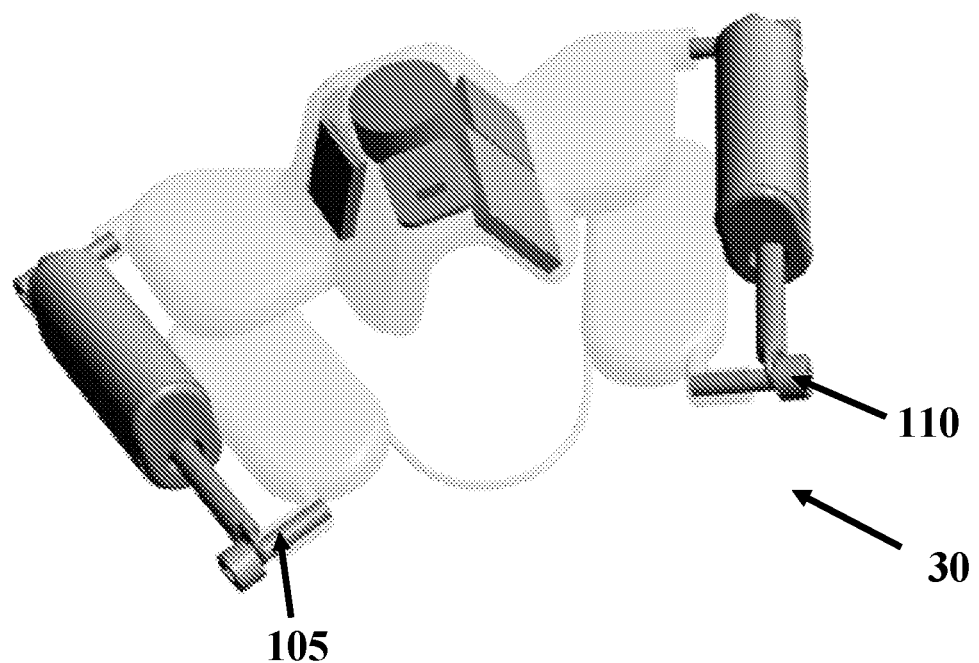
FIG. 2C shows an exemplary lower oral component (30) attached to a front RHS pivot component (105) (via RHS front anchor connector (90)), and a front LHS pivot component (110) (via LHS front anchor connector 95).

FIG. 2A shows an exemplary lower oral component (30) with a RHS lower teeth anchor (80) and a LHS lower teeth anchor (85) connected by a bridge component (100) (e.g., wire). A front anchor connector (90) is attached to (or integral with) the RHS teeth anchor (80), and a LHS front anchor connector (95) is attached to (or integral with) the LHS teeth anchor (85). FIG. 2B shows an exemplary lower oral component (30) attached to a lower set of teeth, as well as a right hand side (RHS) actuator assembly (40) and left hand side (LHS) actuator assembly (45) attached thereto. FIG. 2C shows an exemplary lower oral component (30) attached to a front RHS pivot component (105) (via RHS front anchor connector (90)), and a front LHS pivot component (110) (via LHS front anchor connector 95).

FIG. 3A shows an exemplary upper oral component (20) with a RHS upper teeth anchor (115) and a LHS upper teeth anchor (120) connected by arch component (130). FIG. 3A also shows the RHS rear anchor connector (125) and LHS rear anchor connector (126). FIG. 3B shows an exemplary upper oral component (20) with an arch component (130) containing, or attached to, the following components: i) wireless signal processor (131) (e.g., Bluetooth processor); ii) RHS motor power control processor (132); iii) battery assembly (133) (e.g., composed of a LiPo batter and wireless charging coil/circuit); iv) SpO2 sensor (134); v) LHS motor power control processor (135); and capacitor (e.g., electric double layer capacitor or "EDLC") (136). In certain embodiments, the battery trickle charges the EDLC over a number of seconds (e.g. 30 s) and the charge is monitored by the processor. Once the capacitor is adequately charged the processor instructs the power control unit to dump all the EDLC charge into the motor. This high inrush current develops a magnetic field that increasements the force the motor windings which results in rotation of the motor shaft for a brief period. This process is repeated to advance the shaft position but alternated between the LHS and RHS actuator to keep them synchronized. In some embodiments, the shaft position of each shaft is monitored by encoders within the motor housings. Should a significant discrepancy between the shaft positions occur the processor will pulse one actuate more times than the other actuator until the shaft are once again aligned. In some embodiments, no battery is present and the EDLC capacitor is charged wirelessly and periodically discharged into alternate actuators to initiate movement. In some embodiments the device does not contain an SpO2 sensor, but rather received commands remotely from an ancillary device.

Figure 4A:
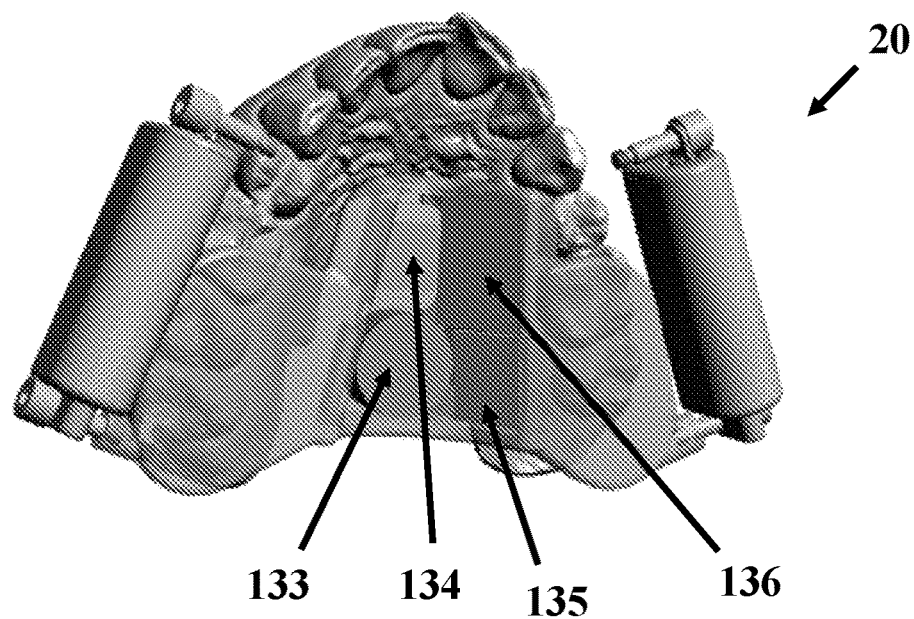
FIG. 4A shows an underside view of an exemplary upper oral component (20) attached to a subject's teeth and having an arch component (130) visibly attached to: i) a battery assembly (133), ii) a SpO2 sensor (134), iii) a LHS motor power control processor (135); and iv) a capacitor (136) (e.g., electric double layer capacitor or "EDLC").
Figure 4B:
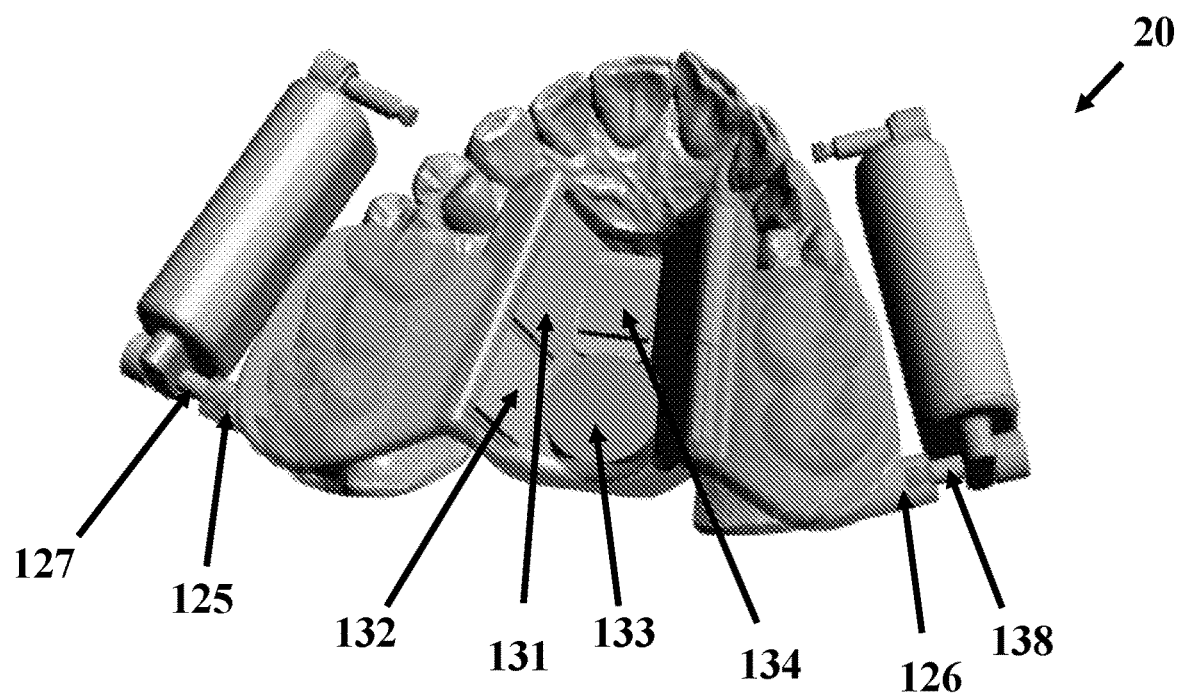
FIG. 4B shows an underside view of an exemplary upper oral component (20) attached to a subject's teeth and having an arch component (130) visibly attached to: i) a battery assembly (133) (e.g., composed of a LiPo batter and wireless charging coil/circuit), ii) a SpO2 sensor (134), iii) a RHS motor power control processor control (132); and iv) a wireless signal processor (131) (e.g., Bluetooth processor).

FIG. 4A shows an underside view of an exemplary upper oral component (20) attached to a subject's teeth and having an arch component (130) visibly attached to: i) a battery assembly (133), ii) a SpO2 sensor (134), iii) a LHS motor power control processor (135); and iv) a capacitor (136) (e.g., electric double layer capacitor or "EDLC"). FIG. 4B shows an underside view of an exemplary upper oral component (20) attached to a subject's teeth and having an arch component (130) visibly attached to: i) a battery assembly (133) (e.g., composed of a LiPo batter and wireless charging coil/circuit), ii) a SpO2 sensor (134), iii) a RHS motor power control processor control (132); and iv) a wireless signal processor (131) (e.g., Bluetooth processor). FIG. 4B also shows a RHS rear anchor connector (125) connected to a rear RHS pivot component, and a LHS rear anchor connector (126) connected to a rear LHS pivot component.

Figure 5A:
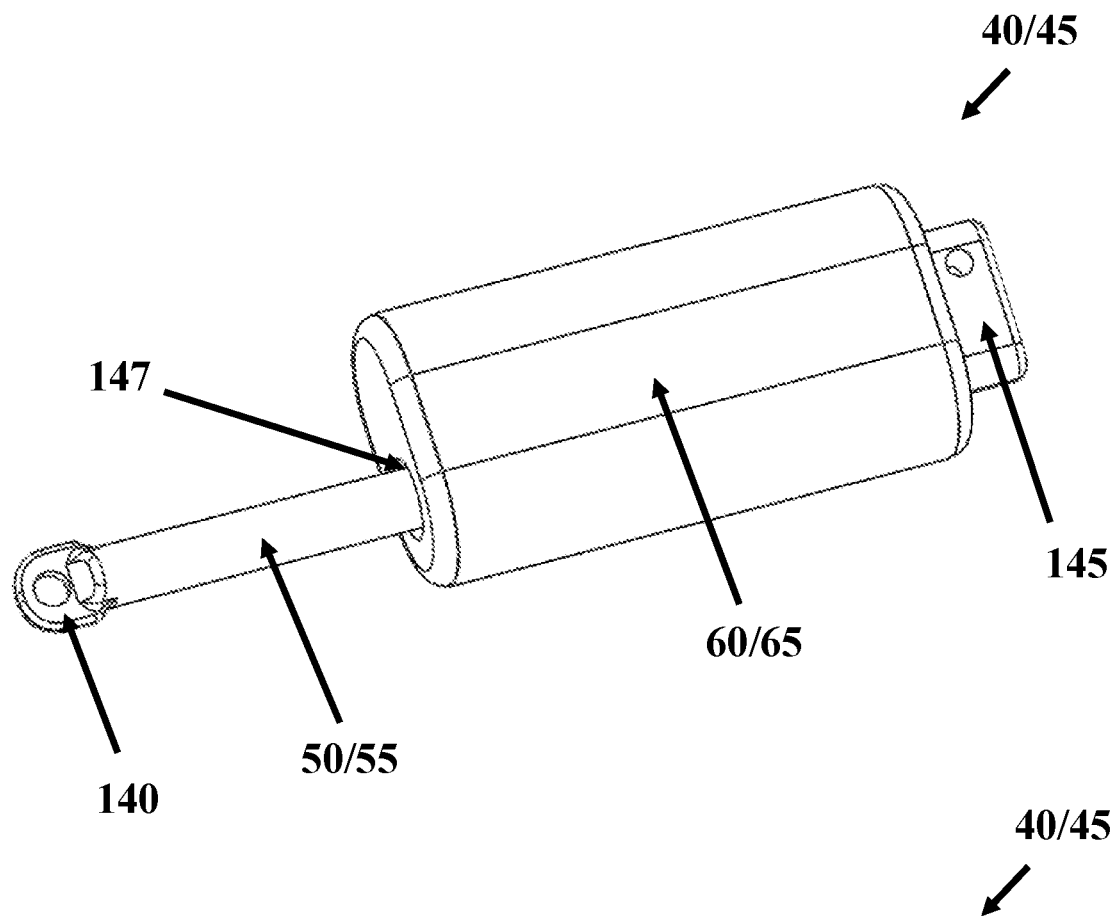
FIG. 5A shows an exemplary right or left hand side actuator assembly (40 or 45) with an extending shaft (50 or 55) in an extended position through the front aperture (147) away from housing (60 or 65). The extending shaft has a shaft connector (140) at the end (e.g., ball joint type connection). The actuator housing (60 or 65) has a housing connector (145) at one end.
Figure 5B:
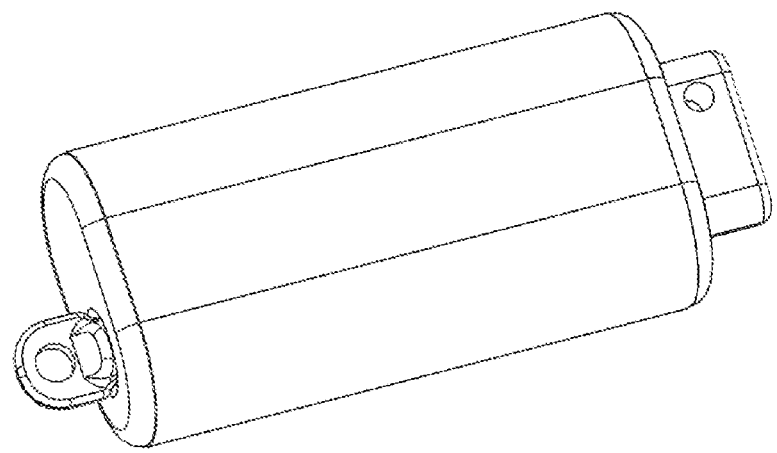
FIG. 5B shows an exemplary right or left hand side actuator assembly (40 or 45) in a non-extended position, such that the extending shaft is fully within the actuator housing (60 or 65).

FIG. 5A shows an exemplary right or left hand side actuator assembly (40 or 45) with an extending shaft (50 or 55) in an extended position through the front aperture (147) away from housing (60 or 65). The extending shaft has a shaft connector (140) at the end (e.g., ball joint type connection). The actuator housing (60 or 65) has a housing connector (145) at one end. FIG. 5B shows an exemplary right or left hand side actuator assembly (40 or 45) in a non-extended position, such that the extending shaft is fully within the actuator housing (60 or 65).

Figure 6A:
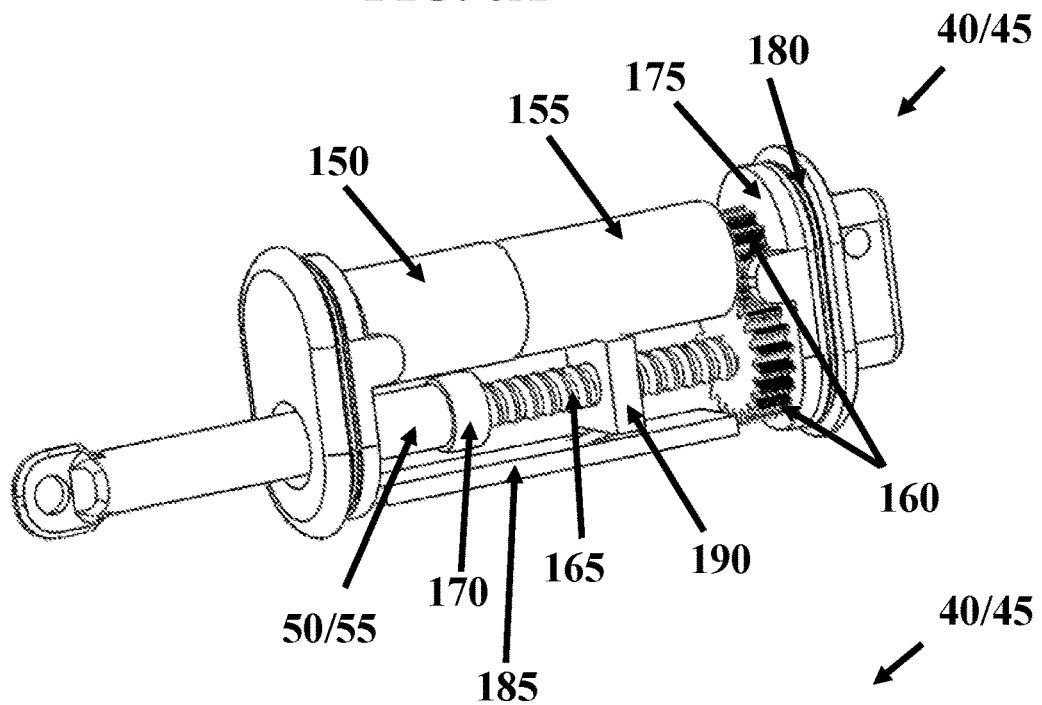
FIG. 6A shows the internal components of an exemplary actuator assembly (40 or 45) with the extending shaft (50 or 55) partially extended out. The internal components of the actuator assembly include: a motor (150) (e.g., DC motor), a gear box (155) (e.g., planetary gear box), gears (160), leadscrew (165), retaining nut (170) to prevent extending shaft (50 or 55) from coming out of housing, thrust bearing/shaft axis support (175), housing O-ring (180), resistive strip (185) (e.g., acts as a potentiometer for absolute position measurement), and leadscrew nut (190) (e.g., to set minimum jaw advancement).
Figure 6B:
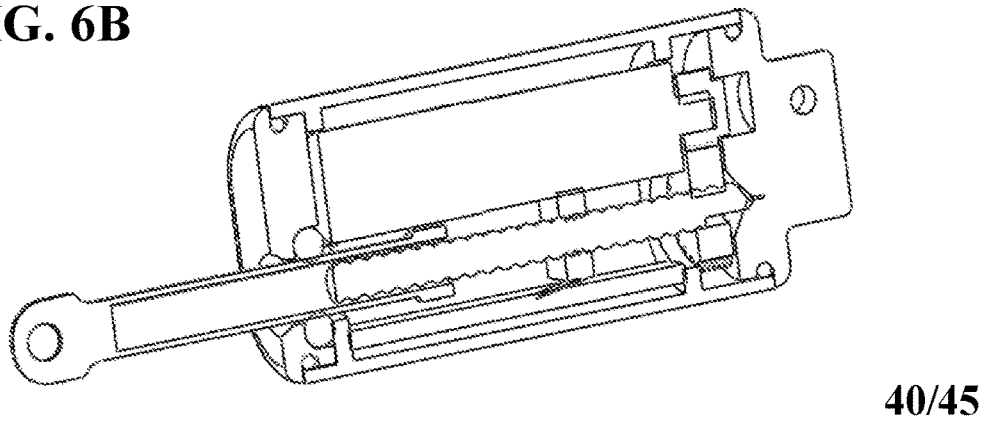
FIG. 6B shows a cut-away view of the actuator assembly in FIG. 6A.
Figure 6C:
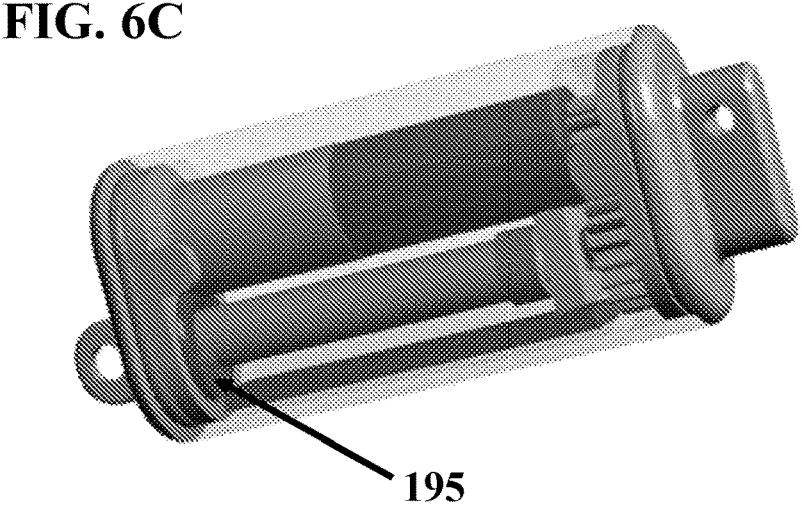
FIG. 6C shows a CAD version of the actuator assembly of FIG. 6A, and further shows a shaft O-ring (195).

FIG. 6A shows the internal components of an exemplary actuator assembly (40 or 45) with the extending shaft (50 or 55) partially extended out. The internal components of the actuator assembly include: a motor (150) (e.g., DC motor), a gear box (155) (e.g., planetary gear box), gears (160), leadscrew (165), retaining nut (170) to prevent extending shaft (50 or 55) from coming out of housing, thrust bearing/shaft axis support (175), housing O-ring (180), resistive strip (185) (e.g., acts as a potentiometer for absolute position measurement), and leadscrew nut (190) (e.g., to set minimum jaw advancement). FIG. 6B shows a cut-away view of the actuator assembly in FIG. 6A. FIG. 6C shows a CAD version of the actuator assembly of FIG. 6A, and further shows a shaft O-ring (195).

REFERENCES

1. US2009/0078273
2. US2014/0135868
3. 2016/0324681
4. 20160324681
5. 20160199215
6. U.S. Pat. No. 8,613,283

All publications and patents mentioned in the above specification are herein incorporated by reference. Various modifications and variations of the described compositions and methods of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the present invention.

We claim:

1. A mandibular advancement system comprising:
   a) an upper oral component comprising:
      i) RHS (right hand side) and LHS (left hand side) upper teeth anchors that are configured to: A) each secure to at least one of a subject's upper teeth, and B) are each attached to, or integral with, an anchor connector,
      ii) an arch component connecting said RHS and LHS upper teeth anchors, wherein the upper teeth anchors are not connected over the labial surfaces of the upper teeth when in use, and
      iii) a plurality of electrical components comprising: A) an energy storage assembly, B) a wireless communications and signal processor, C) at least one motor power control module;
   b) a lower oral component comprising:
      i) RHS and LHS lower teeth anchors that are configured to: A) each secure to at least one of said subject's lower teeth, and B) are each attached to, or integral with, an anchor connector, and
      ii) a bridge component connecting said RHS and LHS lower teeth anchors, wherein the lower teeth anchors are not connected over the labial surfaces of the lower teeth when in use; and
   c) first and second actuator assemblies each comprising:
      i) a housing comprising: A) a plurality of walls defining an internal cavity, B) a front aperture, and C) a housing connector configured to attach to one of said rear anchor connectors directly or indirectly, and
      ii) a plurality of housing components comprising: A) a motor, B) a gear assembly, C) a linear actuator, D) an extending shaft and E) a nut mounted on said linear actuator, and F) a shaft connector operably linked to said extending shaft and configured to attach to one of said anchor connectors directly or indirectly; and
   wherein said mandibular advancement system, when installed in the subject's mouth and when said anchor connectors are attached to said shaft and housing connectors respectively, is configured to move said subject's lower jaw forward past said upper jaw a minimum amount.

2. The system of claim 1, wherein each of said anchor connectors is configured to attach to one of said shaft connectors indirectly via one or more linkage components, and wherein said system further comprises said one or more linkage components.

3. The system of claim 2, wherein said one or more linkage components comprise at least one pivot component.

4. The system of claim 3, wherein said at least one pivot component is selected from the group consisting of: rods, screws, pins, and rings.

5. The system of claim 1, wherein said plurality of electrical components further comprises an oxygen saturation measuring sensor.

6. The system of claim 5, wherein said oxygen saturation measuring sensor comprises a photoplethysmography (PPG) sensor.

7. The system of claim 5, wherein said oxygen saturation measuring sensor is configured to measure oxygen saturation in said subject's soft palate and/or gums.

8. The system of claim 5 wherein said oxygen saturation measuring sensor comprises a pulse oximeter which comprises: a light source, photo detectors, and is configured to transmit light through a translucent, pulsating arterial bed of said subject oral cavity.

9. The system of claim 1, wherein said at least one motor power control module is configured to activate said motors to advance said extending shafts forward when: i) an oxygen saturation measuring sensor detects lower than normal oxygen saturation levels in said subject, ii) an absolute or relative time interval is reached, or iii) a command is received from a remote device.

10. The system of claim 9, further comprising said oxygen saturation measuring sensor, and/or said remote device.

11. The system of claim 1, wherein said at least one motor power control module is configured to activate said motors to allow said extending shafts to retract when: i) an oxygen saturation measuring sensor detects normal oxygen saturation levels in said subject, ii) an absolute or relative time interval is reached, iii) a command is received from a remote device.

12. The system of claim 11, further comprising said oxygen saturation measuring sensor, and/or said remote device.

13. The system of claim 1, wherein said minimum amount is set by a position of each said extending shaft and nut on each said linear actuator, when said extending shafts move away from said respective housing.

14. The system of claim 1, wherein said plurality of electrical components are attached to said arch component, and/or wherein said energy storage assembly comprises a battery assembly.

15. The system of claim 1, wherein each said extending shaft is slidably mounted on said respective linear actuator.

16. The system of claim 1, wherein each said linear actuator comprises a threaded shaft.

17. The system of claim 1, further comprising electrical connectors connecting said plurality of electrical components and said motors, wherein said electrical connectors are selected from: a plurality of wires, cables, circuits, and PCB.

18. The system of claim 1, wherein each said plurality of housing components further comprise a retaining nut attached to said extending shaft that is larger in diameter than said extending shaft and that prevents said extending shaft from fully sliding out of said respective housing.

19. The system of claim 1, wherein said mandibular advancement system, when installed and connected, is further configured to allow said subject to move their lower jaw further forward past said minimum amount, but not allow said subject to withdraw their lower jaw backwards past said minimum amount.

20. A mandibular advancement system comprising:
a) an upper oral component comprising:
  i) RHS (right hand side) and LHS (left hand side) upper teeth anchors that are configured to: A) each secure to at least one of a subject's upper teeth, and B) are each attached to, or integral with, a rear anchor connector,
  ii) an arch component connecting said RHS and LHS upper teeth anchors, wherein the upper teeth anchors are not connected over the labial surfaces of the upper teeth when in use; and
b) a plurality of electrical components comprising: i) a power storage unit, ii) a wireless signal processor, and iii) at least one motor power control processor;
c) a lower oral component comprising:
  i) RHS and LHS lower teeth anchors that are configured to: A) each secure to at least one of said subject's lower teeth, and B) are each attached to, or integral with, a front anchor connector; and wherein the lower teeth anchors are not connected over the labial surfaces of the upper teeth when in use; and
d) first and second actuator assemblies each comprising:
  i) a housing comprising: A) a plurality of walls defining an internal cavity, B) a front aperture, and C) a housing connector configured to attach to one of said rear anchor connectors directly or indirectly, and
  ii) a plurality of housing components comprising: A) a motor, B) a gear assembly, C) a linear actuator, D) an extending shaft, and E) a shaft connector operably linked to said extending shaft and configured to attach to one of said front anchor connectors directly or indirectly; and
wherein said mandibular advancement system, when installed in the subject's mouth and when said front and rear anchor connectors are attached to said shaft and housing connectors respectively, is configured to move said subject's lower teeth forward past said upper teeth a minimum amount when said extending shafts move away from said respective housing.

* * * * *